(12) United States Patent
Chahal et al.

(10) Patent No.: US 11,641,888 B2
(45) Date of Patent: May 9, 2023

(54) SPORTS BRA BUST SUPPORT TESTING

(71) Applicant: Target Brands, Inc., Minneapolis, MN (US)

(72) Inventors: Rajneet Kaur Chahal, North Oaks, MN (US); Gina Marie Cortese, Dallas, TX (US)

(73) Assignee: Target Brands, Inc., Minneapolis, MN (US)

( * ) Notice: Subject to any disclaimer, the term of this patent is extended or adjusted under 35 U.S.C. 154(b) by 230 days.

(21) Appl. No.: 17/179,649

(22) Filed: Feb. 19, 2021

(65) Prior Publication Data

US 2021/0259330 A1 Aug. 26, 2021

Related U.S. Application Data

(60) Provisional application No. 62/981,674, filed on Feb. 26, 2020.

(51) Int. Cl.
*G01M 99/00* (2011.01)
*A41C 3/00* (2006.01)
(Continued)

(52) U.S. Cl.
CPC ............ *A41C 3/0057* (2013.01); *A41C 3/12* (2013.01); *A41D 13/0015* (2013.01); *G01M 99/008* (2013.01)

(58) Field of Classification Search
CPC .... A41C 3/12; A41C 3/0057; A41D 13/0015; G01M 99/008
See application file for complete search history.

(56) References Cited

U.S. PATENT DOCUMENTS

2012/0040588 A1* 2/2012 Steele ................ A41C 3/14
450/74
2018/0368495 A1* 12/2018 Simmons ........... A41D 13/1281
(Continued)

FOREIGN PATENT DOCUMENTS

CN 205072851 U * 3/2016
CN 205072851 U 3/2016
(Continued)

OTHER PUBLICATIONS

Chan et al., Evaluation and Analysis of Bra Design, The Design Journal, An International Journal for All Aspects of Design, vol. 4, Issue 3, Abstract Only, 1 page, 2001.
(Continued)

*Primary Examiner* — Jamel E Williams
(74) *Attorney, Agent, or Firm* — Amanda M. Prose; Westman, Champlin & Koehler, P.A.

(57) ABSTRACT

A method and sensor for testing and evaluating a sports bra for a level of support provided by the sports bra includes selecting a sports bra and removably attaching one sensor to the wearer of the sports bra. The wearer of the sports bra completes an exercise regimen corresponding to a support level indicated for the sports bra and the vertical, lateral and backward/forward movement of a bust supported by or within the sports bra is measured with the single sensor. A largest change in movement in each of the vertical, lateral and backward/forward directions is calculated to determine the level of support actually provided by the sports bra for accurate labeling of the support level of the sports bra for accurately informing consumer purchasing.

20 Claims, 8 Drawing Sheets

(51) Int. Cl.
*A41C 3/12* (2006.01)
*A41D 13/00* (2006.01)

(56) References Cited

U.S. PATENT DOCUMENTS

2019/0301989 A1* 10/2019 Chahal .................... G01N 3/56
2020/0309809 A1* 10/2020 Campbell ........... G01M 99/007

FOREIGN PATENT DOCUMENTS

| | | | |
|---|---|---|---|
| CN | 106723419 A | * | 5/2017 |
| CN | 106723419 B | | 5/2017 |
| KR | 101384761 B1 | | 4/2014 |
| WO | WO-2017126684 A1 | * 7/2017 | ........... A41C 3/0057 |

OTHER PUBLICATIONS

Niemczyk et al., KnE Engineering, DesTech Conference Proceedings, The International Conference on Design and Technology, vol. 2017, 11 pages, 2017.
Starr et al, Biomechanical Analysis of a Prototype Sports Bra, Journal of Textile and Apparel, Technology and Management, vol. 4, Issue 3, 15 pages, 2005.
Zhou et al., Methods of Studying Breast Motion in Sports Bras: a Review, Textile Research Journal, pp. 1-15, 2011.

* cited by examiner

SPORTS BRA BUST SUPPORT TESTING

CROSS-REFERENCE TO RELATED APPLICATION

The present application is based on and claims the benefit of U.S. provisional patent application Ser. No. 62/981,674, filed Feb. 26, 2020, the content of which is hereby incorporated by reference in its entirety.

BACKGROUND

Sports bras are garments that are sturdier than typical bras and provide extra support and protection to a wearer during physical exercise. These garments generally provide support to the bust, or breasts, by way of minimizing breast movement and reducing potential damage to chest ligaments. The level of comfort provided to a wearer by a sports bra can be increased by selecting the appropriate or desired level of support provided by the sports bra.

Sports bras are generally labeled as providing low, medium, or high support. That is, generally a low support supports bra is less restrictive with respect to bust movement than a high support sports bra.

Prior art methods of labeling a sports bra as low, medium, or high support have been arbitrary based on sizing, the elasticity of the material used to form the straps, cups, or back of the sports bra, or by way of the design of the bra and/or straps.

Prior art methods of determining the movement of the bust for purposes of determining support levels required by a sports bar has been limited to physical observation techniques including videotaping subjects during physical activity and viewing the videos to determine what types of movement occurred during running or jogging. These test methods are also limited to determination of vertical bust movement and the corresponding exercises limited to walking, jogging and running.

Studies have been conducted on the need for supportive exercise undergarments which use a multiple sensor system for testing the movement of the wearer in general as well fabric strain during wear and use. However, these sensors have been used in limited form to determine the strain on the fabric and only the vertical or downward direction.

The discussion above is merely provided for general background information and is not intended to be used as an aid in determining the scope of the claimed subject matter. The claimed subject matter is not limited to implementations that solve any or all disadvantages noted in the background.

SUMMARY

A method of testing and evaluating a garment for the physical support provided by the garment includes selecting one or more garments, such as a sports bra for evaluation. The movement of the test subject as actually supported by or supported within the garment is measured. A garment is selected along with a corresponding test subject, where the test subject is selected by way of the garment fitting the test subject comfortably. A sensor or sensor unit is removably secured to the garment. The test subject is then guided through a corresponding exercise regimen consisting of a plurality of dynamic movements. The plurality of dynamic movements include as least two movements different from one another. During the exercise regimen, the sensor measures movement of the portion of test subject supported by or within the garment. The movement is measured along each of an X, Y, and Z axis according to Cartesian coordinates. Testing and evaluation includes calculating a change in position of the supported portion of the test subject along each of the X, Y, and Z axis during the exercise regimen and assigning a support value to the garment based on at least one change value calculated.

According to one embodiment, the garment is a sports bra or other article of clothing worn to provide support to the wearer's bust during physical exercise. Bust movement during the exercise regimen is measured for determining whether the support value provided to the bust of the wearer of the sports bra is actually low, medium, or high.

The X axis correlates to side to side movement of the bust, the Y axis correlates to vertical movement of the bust, and the Z axis correlates to backward and forward movement of the bust, with respect to a torso of the test subject.

According to one embodiment, the corresponding exercise regimen includes one or more of a warm-up exercise regimen, a low support exercise regimen, a medium support exercise regimen, and a high support exercise regimen wherein movement is measured by the sensor continuously during the corresponding regimen. The regimen may be selected based on an initial support level assigned to the sports bra for confirmation of the support level.

According to one embodiment, the corresponding exercise regimen includes a medium support exercise regimen and the sports bra is a "cut and sew" sports bra construction.

Calculating movement of the bust comprises calculating a greatest change in measured position along each of the X, Y, and Z axis and assigning a support value to the sports bra is based on at least one greatest position change value calculated. A "low support" sports bra is one where the test resulted in a greatest change value along at least the Y axis of greater than about 200. A "medium support" sports bra is one where the test resulted in a greatest change value along at least the Y axis in the range of about 100 to 200. A "high support" sports bra is one wherein the greatest change value along at least the Y axis is less than about 100.

According to one embodiment where the sports bra is a seamless style sports bra, a "low support" sports bra is one where the test resulted in a greatest change value along at least the Y axis of greater than about 300. A "medium support" sports bra is one where the test resulted in a greatest change value along at least the Y axis in the range of about 150 to 300. A "high support" sports bra is one wherein the greatest change value along at least the Y axis is less than about 150.

In accordance with a further embodiment, a method of testing and evaluating a sports bra for a level of support provided by the sports bra includes selecting a sports bra and removably attaching one sensor to a wearer. The sensor is placed in contact with the user at an upper portion of a left cup of the sports bra such that the strap of the sports bra may hold the sensor in place in contact with the wearer. The sensor is placed between the strap and the wearer's skin. The wearer is guided through a selected exercise regimen corresponding to a first support level indicated for the sports bra while the sensor collects data related to the vertical, lateral and backward/forward movement of a bust supported by or within the sports bra. A largest change in movement in each of the vertical, lateral and backward/forward directions throughout the exercise regimen is calculated for determining if the first support level indicated for the sports bra is accurate. Updating the support level to a second support level is indicated wherein in the second support level is more accurate than the first support level and is based in part upon the calculated change in movement in at least one of the vertical, lateral and backward/forward directions.

According to one embodiment, the exercise regimen corresponding to the first support level is one of a low support regimen, a medium support regimen, or a high support regimen. The exercise regimen may also include a warm-up regimen.

According to one embodiment, each of the low support regimen, medium support regimen, and high support regimen comprise a plurality of dynamic movements wherein at least two of the plurality of dynamic movements in any regimen are different moves. Each of the low support regimen, medium support regimen, and high support regimen comprise transitions between each dynamic move of a plurality of dynamic moves where the transitions comprise in the range of about 0 to about 15 seconds of rest.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DETAILED DESCRIPTION

Figure 1:
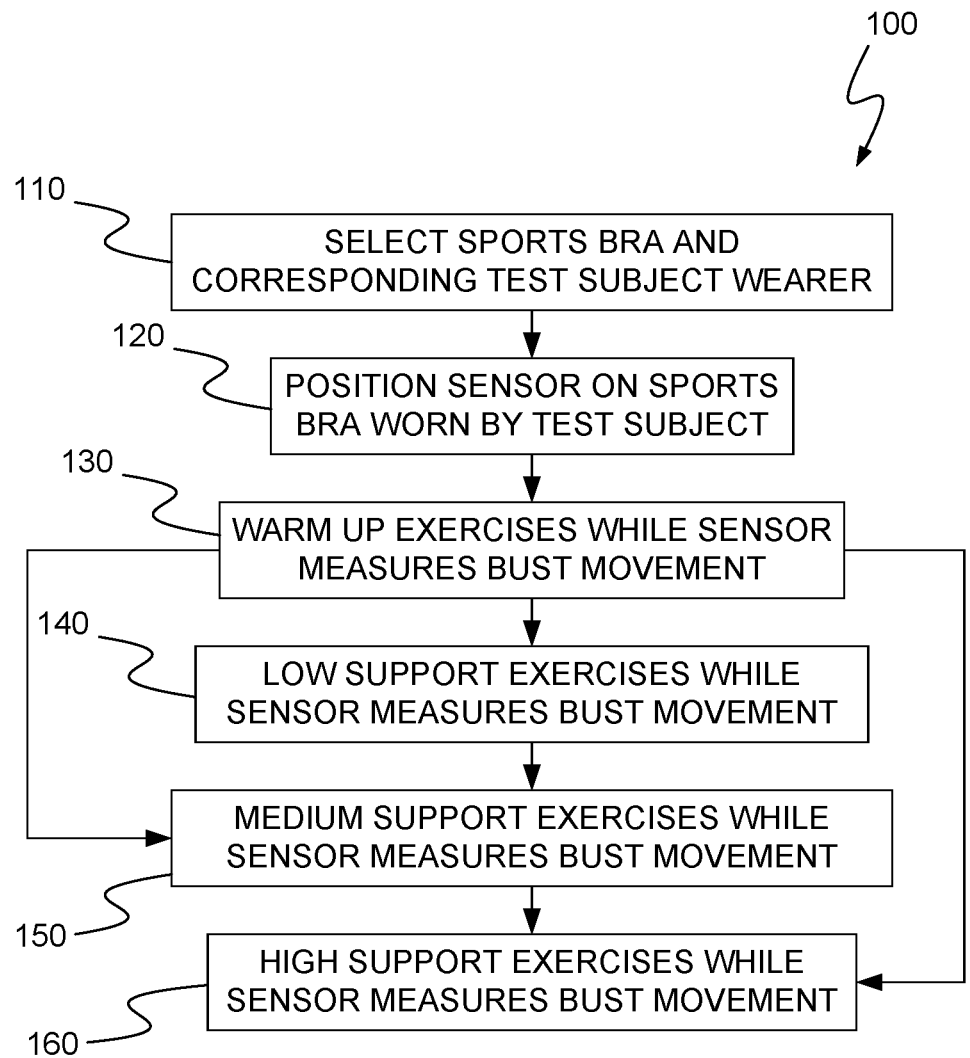
FIG. 1 is a flow diagram of a method of performing a garment support testing method on one or more sample garments.

Sports bras are garments worn to provide physical support to the bust of a wearer. The bust support provided by a sports bra is due in part to the material from which the garment is constructed as well as the construction design of the garment. Sports bras provide a level of bust support generally referred to as "low," "medium," or "high" when worn. Sports bra wearers may also independently prefer a low, medium, or high level of support depending at least in part on desired comfort, activities to be carried out when wearing the sports bra, the wearer's physical size and/or body type and/or bust size. However, there is a lack of consistency and notice to the purchaser when actually selecting a sports bra. Trying a selected bra on does not provide an accurate indication of the support provided when in use across different sizes of bra. Inaccurate labeling of sports bras can result in purchase of a sports bra that causes injury to the wearer and/or discomfort which diminishes the returns from physical exercise for the wearer.

Embodiments described below increase the accuracy and consistency of the determination of the level of support provided by selected sports bras to eliminate confusion or misconception when purchasing a selected garment.

In accordance with one embodiment, a single sensor or single sensor unit is placed on the selected bra and the sensor is configured for detecting and monitoring bust movement as controlled by the sports bra when worn by a user. The users completes a set of various exercises which include dynamic body movements and which may be in addition to walking, jogging, or running to mimic the movement of the wearer during exercise. The extent of the bust movement occurring while wearing the sports bra during exercises is measured in order to determine the amount of or restriction, or lack thereof, of the bust, in one or more directions. The change in bust position, or movement, in each direction is correlated to a low, medium, or high level of support offered by the sports bra. The determination of low, medium, or high support may also be distinguished based on or otherwise correspond to sports bra sizes.

Bust movement is sensed in a vertical or up and down direction, lateral or side to side direction, and compression or backward/forward direction, to provide an improved indicator of the level of support to the wearer's bust as provided by the sports bra.

As used throughout the specification, what is meant by "sports bra" is a garment worn to support the bust of the wearer during physical exercise. Sports bras are sturdier than standard bras and minimize bust movement when worn.

Generally, it is desirable for a sports bra to reduce movement of the bust and also alleviate discomfort during physical exercise while reducing potential damage to chest ligaments. These garments are marked by the manufacturer with various identifiers, including most commonly as offering a "high," "medium," or "low" level or support. As the user selects the desired support level based on numerous personal preference factors which include comfort during the performance of physical exercise, the indicated level of support must be accurate to prevent discomfort or injury to the wearer as most wearers would not become aware of the misidentification of the level of support until after wearing the garment during physical exercise.

The methods described herein are used to test and evaluate the support provided by a garment such as a sports bra. While the embodiments described herein refer to a sports bra, any like garment worn on the bust and configured to provide coverage and/or support of any level to the wearer's bust can be tested and evaluated according to the methods and devices described here. Additionally, the garments may be constructed of any one or more textiles and other materials and have any one or more styles or configurations for wearing. That is, no single style or construction of sports bra or garment is more appropriate or preferred for testing according to the methods and devices described herein than another, different make or style.

FIG. 1 provides a flow diagram for a sports bra support test method according to an embodiment described herein. The sports bra support test of the embodiment described herein includes removably attaching a sensor to a location on the sports bra as the bra is worn by a test subject. The test subject then is directed through a series of movements including optionally a set of warm up exercises, followed by at least one of a set of low support exercises, medium support exercises, and high support exercises. During selected exercises, the sensor measures data based on the extent of movement of the bust as described further below. The measured movement during the course of exercise is recorded and can be used to evaluate the actual level of support provided by the selected sports bra as provided by the flow diagram for evaluation illustrated in FIG. 8.

The measurement of movement of the bust according to the embodiment described herein includes positioning a single sensor configured to measure the change in position or movement of the bust along the X, Y, and Z axis according to a Cartesian coordinate system. For example, side to side or lateral movement of the bust supported by or within the sports bra is indicated by movement on an X axis, vertical movement of the bust is indicated by movement on a Y axis, and backward-forward movement of the bust is indicated by movement on a Z axis. The movement being measured in the three directions described above by the sensor or sensor unit is hereinafter also referred to generally as "bust movement." The change in position or bust movement is measured according to displacement in one or more directions from a starting position, such as a pre-exercise, standing position with the sports bra on the test subject.

In further detail, the embodiment described in FIG. 1 is a method 100 of dynamic exercise testing of a sports bra. A sports bra is selected for testing and evaluation and a corresponding test subject is selected at step 110. The test subject may generally be a wearer of a sports bra of the same cup or overall size as the selected sports bra, for a corresponding correct fit of the sports bra on the wearer. Ensuring that the sports bra fits the test subject may increase the accuracy of the testing and evaluation of the support provided by the sports bra. Testing and evaluation according to the embodiments herein where the selected sports bra is too small or too large for the test subject will result in inaccurate movement readings that do not correlate as accurately to the sports bra.

Once the sports bra and corresponding test subject are matched and selected, a sensor is removably secured to the sports bra on an uppermost area of the left cup portion of the sports bra at step 120. In accordance with one embodiment, the sensor is removably secured on the uppermost portion of the left cup, just below the left strap, such that the sensor is positioned as high on the cup as possible without being secured to the strap.

Figure 2:
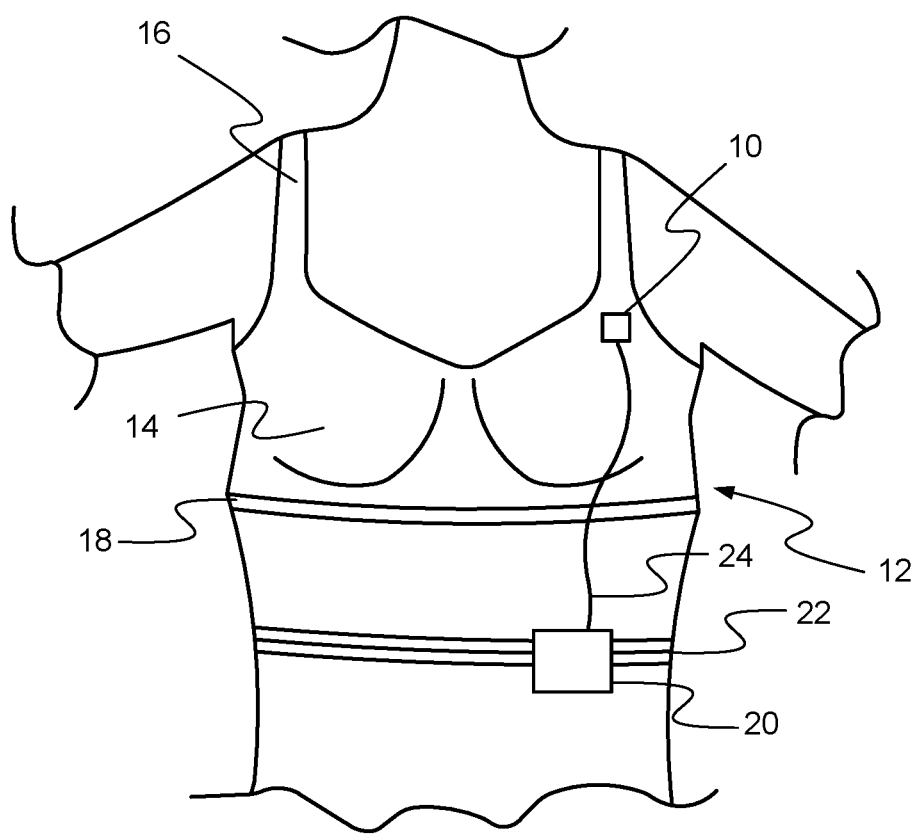
FIG. 2 illustrates a test subject wearing the garment for testing and corresponding testing equipment.
Figure 3:
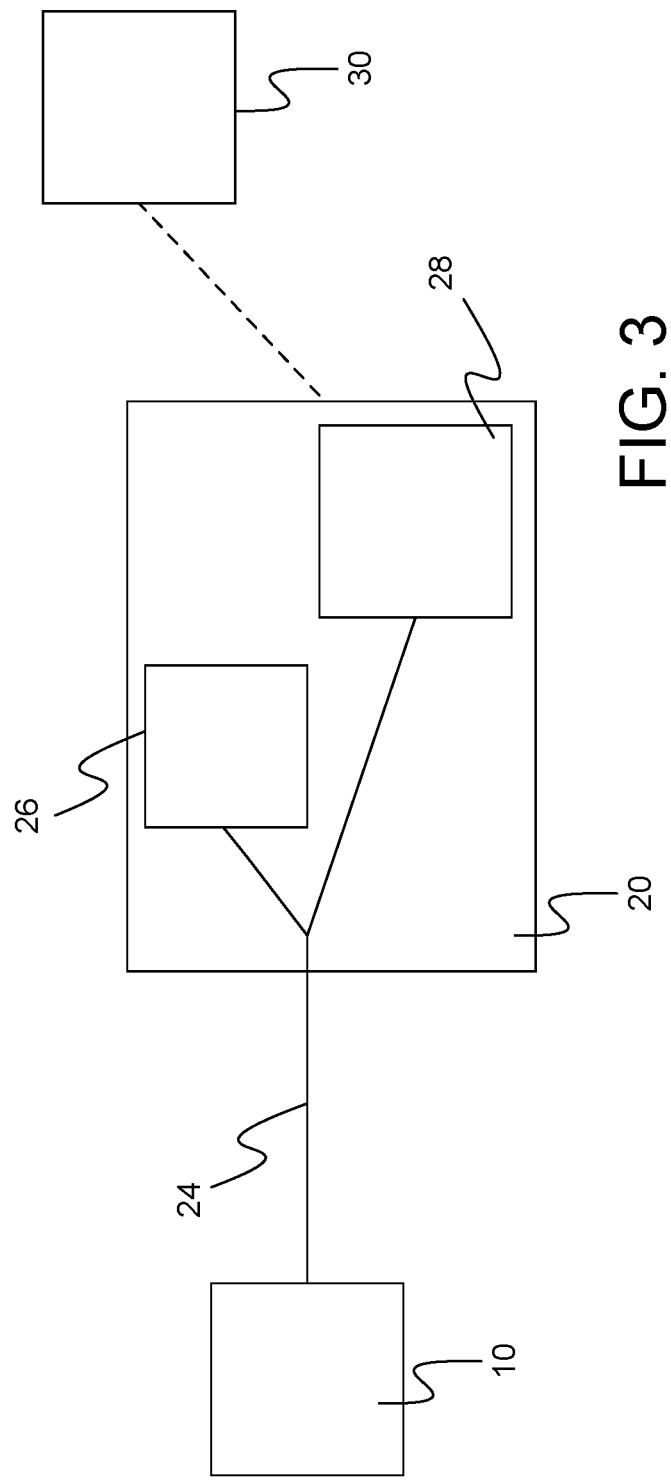
FIG. 3 is a block diagram of a sensor system for measuring bust movement when a garment is worn during support testing.

The sensor may be a device 10 as described herein and illustrated in FIGS. 2 and 3. For example, at step 130 the test subject may carry out one or more warm up exercises while the sensor measures the bust movement during these exercises. At step 140 the test subject then carries out a series of support exercises while the sensor continues to measure the bust movement during these exercises. For example, the exercise regimen of step 140 comprises exercises tailored for "low" support sports bras. Additionally or alternatively, the test subject then may carry out the exercise regimen for medium support sports bras at step 150 and further additionally or alternatively the high support sports bras exercise regimen at step 160 while bust movement is continuously measured during each stage of exercise.

The dynamic exercises of each of steps 140, 150, and 160 are selected based on the movements requiring low, medium, or high support sports bras for the wearer. The methods described herein may comprise a dynamic movement regimen such as the low support exercise regimen at step 140 when testing a sports bra for low support; the medium support exercise regimen at step 150 when testing a sports bra for medium support; or the high support exercise regimen at step 160 when testing a sports bra for high support. One support level exercise regimen may be carried out for testing. Additionally or alternatively, the warm-up regimen of step 130 may be carried out before any one or more of the regimens at steps 140, 150, 160. It is also contemplated that in one embodiment of the methods described herein one or more of the regimens of steps 130, 140, 150, and 160 may be carried out in succession or across a plurality of testing sessions for testing of the selected sports bra.

Figure 4:
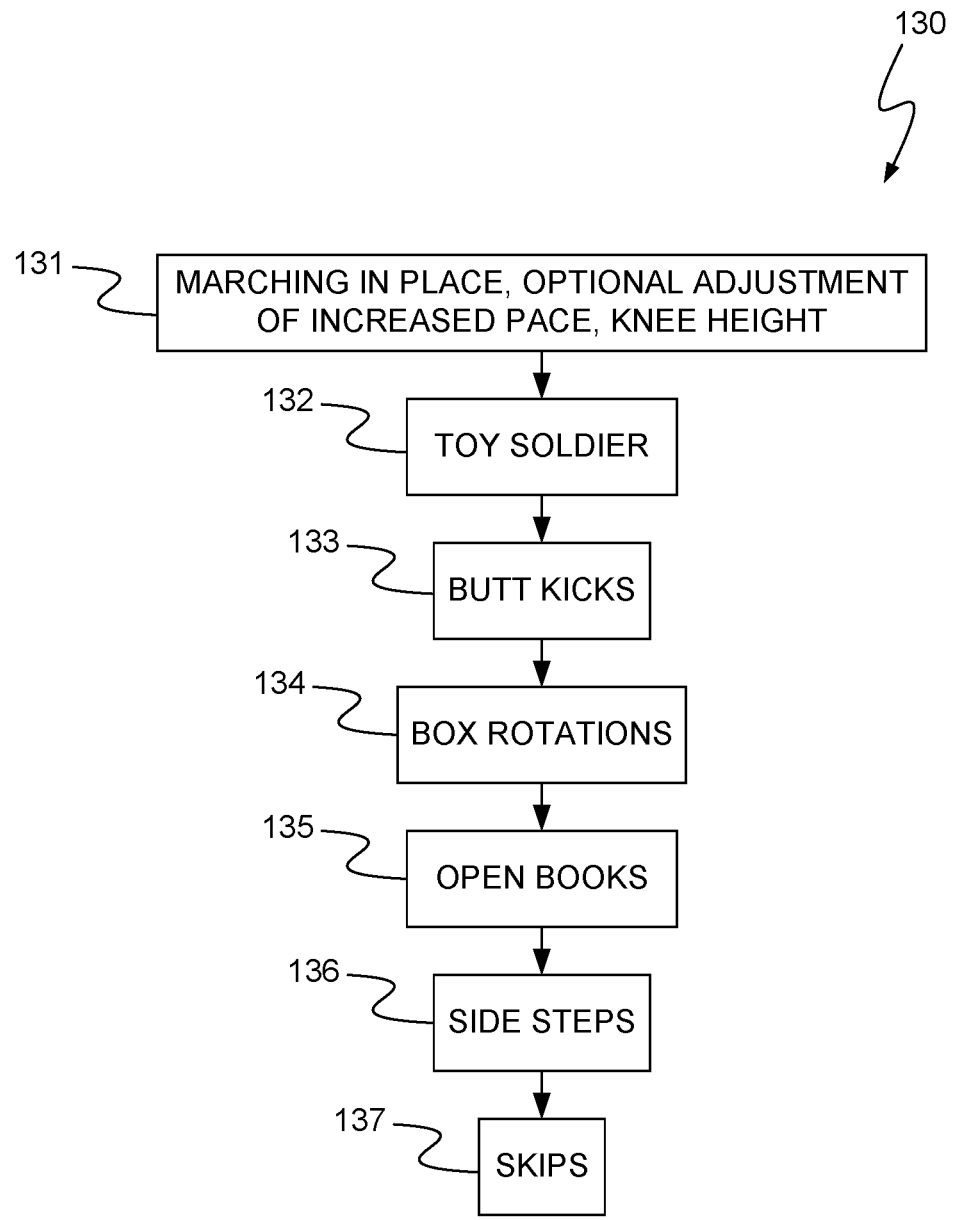
FIG. 4 is a flow diagram of a warm-up exercise progression of the method of performing the garment support testing.

In one embodiment of the dynamic exercise testing of a sports bra as illustrated in the flow diagram of FIG. 4, the warm up exercises of step 130 may include marching in place at step 131 with an optional amplification by increasing the tempo and/or height of the knee raise, toy soldiers at step 132, butt kicks at step 133, box rotations at step 134, open books at step 135, side steps at step 136 and skips at 137.

Figure 5:
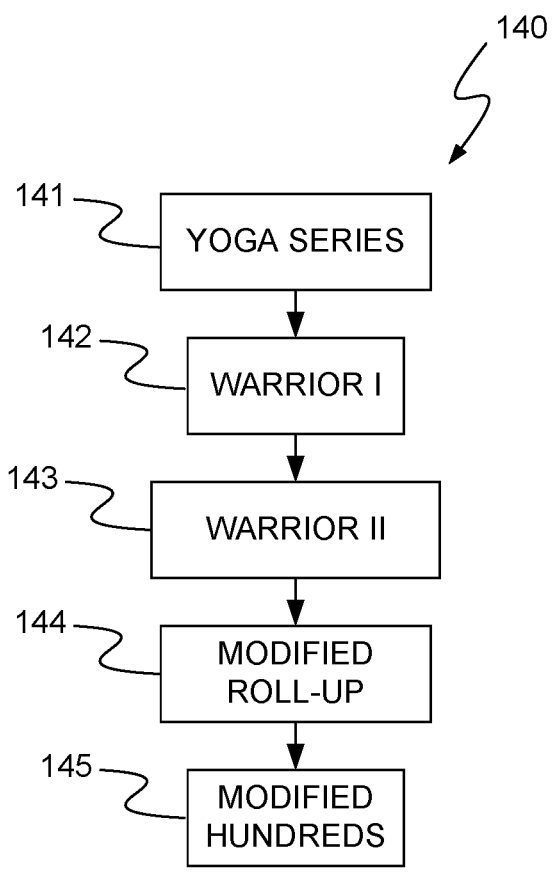
FIG. 5 is a flow diagram of a low support exercise progression of the method of performing the garment support testing.

In one embodiment of the dynamic exercise testing of a sports bra as illustrated in the flow diagram of FIG. 5, the low support exercise regimen of step 140 may include a yoga series at step 141 including, for example, a sun salutation to warrior I at step 142 and then warrior II at step 143, followed by a modified roll up at step 144 and modified hundreds at step 145. Additional or alternative options for movements in the low support exercise step 140 of the test 100 include but are not limited to walking and/or the replacement of one or more warrior poses with a child's pose or the addition of a child's pose to the sun salutation. Pilates moves such as the bird dog, which further challenges the effect of gravity on bust tissue and the sports bra can be incorporated. Stretches for the chest area including upper back stretches, posterior deltoid stretch, standing lateral stretch, and/or knees to chest may also be included.

Figure 6:
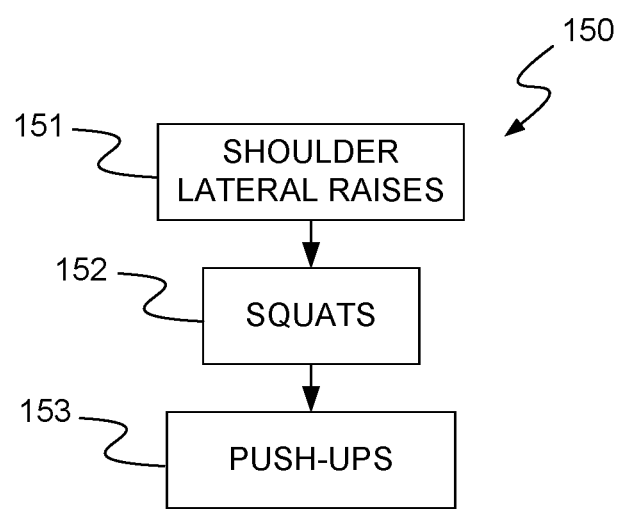
FIG. 6 is a flow diagram of a medium support exercise progression of the method of performing the garment support testing.

In one embodiment of the dynamic exercise testing of a sports bra as illustrated in the flow diagram of FIG. 6, the medium support exercise regimen of step 150 may include shoulder lateral raises at step 151, squats at step 152, and push-ups at step 153. Additional or alternative options for movements in the medium support exercise step 150 of the dynamic exercise testing of a sports bra include but are not limited to the incorporation of moves including hand and resistance weights, exercise balls or other equipment.

Figure 7:
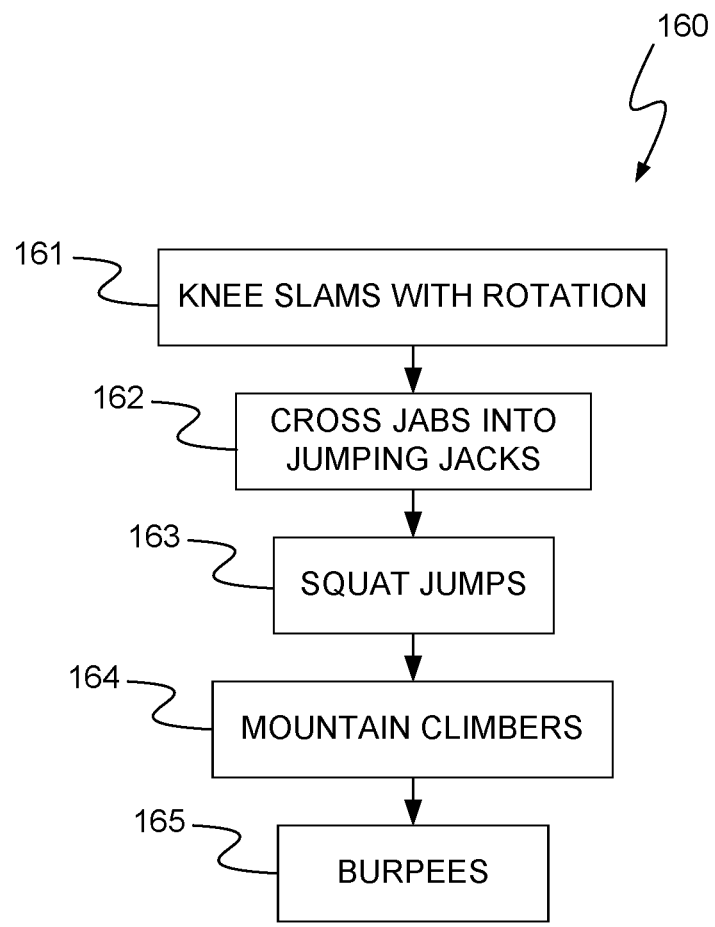
FIG. 7 is a flow diagram of a high support exercise progression of the method of performing the garment support testing.

In one embodiment of the dynamic exercise testing of a sports bra as illustrated in the flow diagram of FIG. 7, the high support exercise regimen of step 160 may include knee slams with rotation at step 161, cross jabs into jumping jack sequences at step 162, squat jumps at step 163, mountain climbers at step 164 and burpees at step 165. Additional or alternative options for movements in the high support exercise step 160 of the test 100 include but are not limited to the replacement of one or more moves such as squat jumps with skaters or other lateral high impact movements.

The dynamic exercise testing of a sports bra comprises regimens at steps 130, 140, 150, and/or 160 selected based on the alleged, desired, or selected support level offered by the sports bra and may serve to confirm the level of support offered by the sports bra or update the identification of the level of support of the sports bra. However, it is within the scope of this disclosure that embodiments of the method 100 may include one or more regimens 130, 140, 150, and/or 160 and the order of such exercises may be altered based on the selected sports bra and/or test subject. Further, while the exercise moves within each regimen defined at steps 130, 140, 150, and 150 are provided in an order of sub-steps (e.g., 131, 132, etc.) the embodiments described herein are not so limited such that alterations to the order of steps illustrated in FIGS. 4-7 may be altered and/or specific moves may be replaced with movements of the same or similar support level.

Referring back to FIGS. 2 and 3, which illustrate the sensor or sensor unit 10 worn by the test subject during the test method 100 and for measuring bust movement during the exercises, the sensor or sensor unit 10 is a small sensor that is removably secured to the test subject. The sensor itself may be in contact with the skin of the test subject and held in place on the test subject via a strap of the sports bra 12. In some embodiments, the sensor 10 can be secured via a magnetic clip with one magnet fixed to the sensor such that a pair of magnets will removably secure the sensor to the fabric of the sports bra 12. However, in the embodiment illustrated, the left strap of the sports bra retains the sensor in position on the test subject by providing a compressive force to hold the sensor in contact with the test subject.

The methods described herein require only a single sensor or single sensor unit 10 positioned on an upper left shoulder area of test subject and in contact with the strap of the sports bra 12 worn by the test subject. For example, the sensor 10 may be removably secured to the sports bra 12 at a location on the uppermost portion of the left cup 14 of the bra 12, just below the left strap 16, such that the sensor is positioned as high on cup 14 as possible without being secured to strap 16. Such positioning has been found to provide the most accurate measurements of each of the bust movement directions measured including lateral, vertical, and backward/forward movement.

Sensor 10, also referred to interchangeably herein as sensor unit 10, is connected to a control box 20 which is worn around the waist of the test subject by a flexible strap 22. Strap 22 adjusts to fit snugly around the test subject and to hold control box 20 comfortably in position on the test subject.

Sensor unit 10 may be a sensor such as a multi-axis position sensor, a displacement sensor, an accelerometer, or a gyroscope for example. In one embodiment, the sensor unit 10 is a displacement sensor such as a capacitive displacement sensor, which is a non-contact sensor capable of high-resolution measurement of the position and/or change of position of the target in each of the directions described herein. In the embodiment where the sensor unit 10 is a multi-axis position sensor the sensor may be an absolute position sensor.

Sensor 10 is operably connected to the contents of control box 20 via one or more wires 24. Control box 20 is a lightweight housing that protects the inner contents from any sweat or other liquids it may be exposed to during use. The control box 20 may be formed by various methods including three-dimensional (3D) printing of a lightweight thermoplastic material, injection molding or other like methods.

Control box 20 supports a battery 26 for providing power to the sensor 10. The battery is a lightweight battery and rechargeable as well as disposable batteries may be used. A control board 28 is also positioned within the control box 20 and is operably connected to the sensor 10. The control board 28 receives measurements from the sensor 10 and relays these measurements via a wireless connection to a controller 30. In one embodiment the wireless connection is a Bluetooth connection or a WiFi connection. Controller 30 comprises software for receiving and displaying the measurements. As illustrated in FIG. 2, control box 20 is also removably secured to the test subject at a location away from the sports bra such that control box 20 and its strap as well as contents and sensor connections do not hinder or support the area adjacent to or the sports bra itself.

Figure 8:
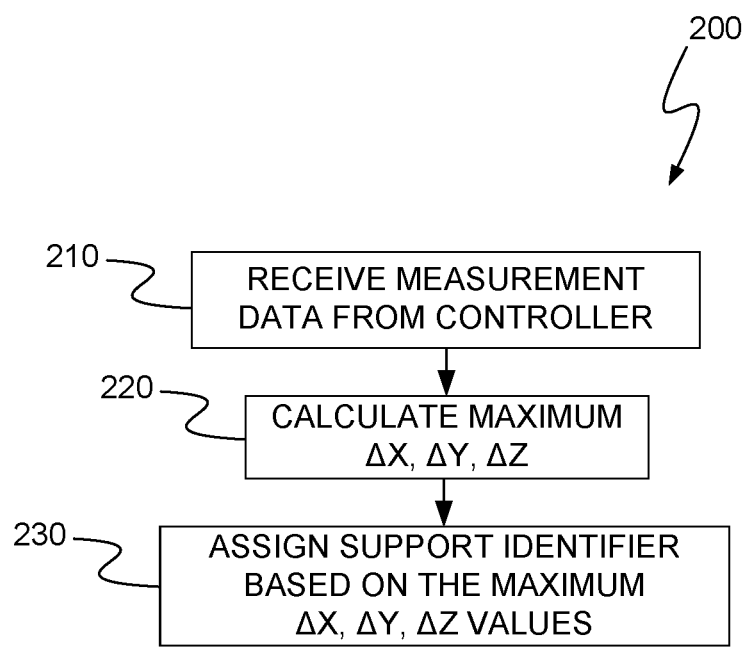
FIG. 8 is a flow diagram of a method of evaluating the garment support testing method for determining a support level corresponding to the garment.

In further detail, the embodiment described in FIG. 8 is a method 200 of evaluating the dynamic exercise testing carried out in method 100 and providing a label to the selected sports bra to accurately reflect the level or support provided to wearers of the selected sports bra. The controller 30 receives the measurement data from the sensor 10 at step 210. The highest and lowest displacement values can be selected for each direction of movement (x, y, or z) and thus a maximum change in position for these values calculated at step 220. At step 230 a label of "low," "medium," or "high" support is assigned to the sports bra. In testing sports bras referred to as "cut and sew" style (meaning the bras have seams) the indicator of "low" support is provided to those sports bras with a $\Delta X$, $\Delta Y$, and $\Delta Z$ above about 200 as this corresponds to a greater extent of movement of the bust during exercise while supported by the selected bra. A "medium" support indicator is provided to those sports bras with a $\Delta X$, $\Delta Y$, and $\Delta Z$ in the range of about 100 to 200. A "high" level of support indicator is provided to those sports bras with a $\Delta X$, $\Delta Y$, and $\Delta Z$ less than about 100 as this correspondence to lower extent of movement of the bust during exercise while supported by the selected bra.

In testing sports bras referred to as "seamless" style (meaning the bras do not have seams) the indicators for "low," "medium," and "high" support may have increased ranges. The indicators of support are provided in the same manner such that the indicator is based on a sports bra with a $\Delta X$, $\Delta Y$, and $\Delta Z$ value, however that value may be about 250, above about 300 or more as this corresponds to a greater extent of movement of the bust during exercise while supported by the selected seamless bra. A "medium" support indicator may then be provided to those sports bras with a $\Delta X$, $\Delta Y$, and $\Delta Z$ in the range of about 150 to 250, or 200 to 300, or higher. A "high" level of support indicator may then be provided to those sports bras with a $\Delta X$, $\Delta Y$, and $\Delta Z$ less than about 150 or less than about 250, as this correspondence to lower extent of movement of the bust during exercise while supported by the selected seamless bra.

It is also contemplated that the most significant factor for comfort and support, perceived or actual, by wearers of sports bras is the restriction of vertical movement (e.g., $\Delta Y$), thus, in testing where the $\Delta X$, $\Delta Y$, and $\Delta Z$ values are not all in the same range corresponding to "low," "medium," or "high" support, the value of $\Delta Y$ may override the other values to provide the final reference to a selected support level indicator.

It is also contemplated that while the movement along the X, Y, and Z axis described herein is used to provide a single indicator of support, these values can be used to provide further labeling information for ease of selection of an appropriate sports bra for a wearing by indicating levels of support in each of the directions individually. Such additional detailed information may be advantageous where a wearer is concerned about specific movement in the X, Y, or Z directed and a corresponding level of support. This information may also be advantageous where the level of support may differ between "low," "medium," and "high" for the same sports bra with respect to movement in different directions.

ILLUSTRATIVE EXAMPLES

In one example, the dynamic exercise testing of a sports bra was carried out according to one or more of the regimen specifications listed in TABLES 1-3 below.

TABLE 1

| | (Step 140, low support exercise regimen) | | | | |
|---|---|---|---|---|---|
| Type | Exercise | Guidelines | Time | Special Notes | Assess/Challenge |
| Cardio | Walk | 3.0-3.5 mph 0% incline | 2 min | RPE 1-10: 3-4; time includes getting up to speed as well as time it takes to stop | Light Continuous Movement |
| Yoga | Sun Salutation Series | | ~45 sec | 15 second transition | Yoga Series |
| Yoga | Warrior I to Warrior II Series | 1× each leg leading | Hold each pose 15 sec; 1 minute total | No transition | Yoga Standing Static Pose with Arm Movement |
| Pilates | Half Roll | 5 repetitions | ~45 sec | 10 second transition | Pilates Seated Exercise with Core Movement |
| Pilates | Hundreds | 5 breaths | ~30 sec | 5 second transition | Pilates Lying Exercise with Arm Movement |
| Total Time | | | ~5 min 30 sec | | |

TABLE 2

| | (Step 150, medium support exercise regimen) | | | | |
|---|---|---|---|---|---|
| Type | Exercise | Guidelines | Time | Special Notes | Assess/Challenge |
| Cardio | Power Walk | 4.0-4.5 mph | 1 min 30 sec | | Moderate Impact Continuous Movement |
| Cardio | Hike | 3.0-3.5 mph 12% grade | 1 min 30 sec | 30 second transition to resistance exercises | Moderate Impact Continuous Movement |
| Resistance | Lateral Raise with Tubing | 10 repetitions | ~30 sec | | Upper Body Resistance /Gym Like Activity with Equipment |
| Resistance | Bodyweight Squat | 10 repetitions | ~30 sec | 15 second transition | Lower Body Resistance/Gym Like Activity |
| Resistance | Bodyweight Push Up | 10 repetitions | ~30 sec | | Upper Body Resistance /Gym Like Activity |
| Total Time | | | ~5 min 30 sec | | |

TABLE 3

| | (Step 160, high support exercise regimen) | | | | |
|---|---|---|---|---|---|
| Type | Exercise | Guidelines | Time | Special Notes | Assess/Challenge |
| Cardio | Run | 5.0-6.0 mph | 1 min 30 sec | Includes time to get treadmill up to speed | |
| Aerobic/Dance | Knee Slams with Rotation | | 30 sec | 30 second transition from treadmill | Simultaneous Arm and Leg Movement with Vertical Displacement |
| Aerobic/Dance | 4 Punches to 4 Jacks Sequence | Punch on each arm equals 1 | 30 sec | no transition | Cross Chest Movement With Lateral Impact Movement |
| HIIT | Squat Jump | | 30 sec | 15 second transition | Vertical Movement |
| HIIT | Mountain Climbers | | 30 sec | 15 second transition | Movement in Horizontal/Bent Over Position |

TABLE 3-continued (Step 160, high support exercise regimen)

| Type | Exercise | Guidelines | Time | Special Notes | Assess/Challenge |
|---|---|---|---|---|---|
| HITT | Burpees | | 30 sec | | Vertical Movement into Horizontal |

TABLE 4

Test Results for various pre-manufactured sports bra

| # | Support Regimen | Sample Desc. | Size | ΔX (side to side) measured | ΔY (up and down) measured | ΔZ (back and forward) measured | Support Label after testing |
|---|---|---|---|---|---|---|---|
| 1 | Low | Light support without pads | Small | 169/54 223 | 155/53 208 | 236/103 339 | Low |
| 2 | Low | Light support without pads | Large | 126/336 462 | 344/260 604 | 127/114 241 | Low |
| 3 | Low | Strappy long line with removable pads | Large | 78/139 217 | 117/189 306 | 82/237 319 | Low |
| 4 | Medium | Strappy Fashion | Small | 67/60 127 | 70/68 138 | 40/128 168 | Medium |
| 5 | Medium | bonded racer | Small | 60/47 107 | 54/53 107 | 41/123 164 | Medium |
| 6 | Medium | bonded racer | Small | 52/51 103 | 84/48 132 | 61/114 175 | Medium |
| 7 | Medium | v-back wide strap bra | | 41/44 85 | 67/57 124 | 33/96 129 | Medium |
| 8 | Medium | v-back wide strap bra | Large | 61/67 128 | 80/112 192 | 102/106 208 | Medium |
| 9 | Medium | Shape bra with mesh | | 171/69 240 | 113/65 178 | 44/94 138 | Medium |
| 10 | High | Convertible (tested on medium protocol) | Small | 126/80 206 | 86/76 162 | 98/265 363 | Medium |
| 11 | High | Convertible (tested on medium protocol) | Small | 118/85 203 | 93/76 169 | 41/123 164 | Medium |
| 12 | High | Convertible (tested on medium protocol) | Large | 67/77 144 | 125/85 210 | 49/78 127 | Medium to Low |
| 13 | High | front zip bra (tested on medium protocol) | 34B | 48/40 88 | 58/37 95 | 33/130 163 | High |

As can be seen from the samples tested above and the results in TABLE 4, at least sample numbers 3, 8, 9, and 14-19 were originally labeled by the manufacturer with inaccurate support identification. It appears that the largest area of misidentification relates to the so-called "high" support bras.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms for implementing the claims.

What is claimed is:

1. A method of testing and evaluating a garment for a level of support provided by said garment, the method comprising:
   selecting a garment and a corresponding test subject for said garment;
   removably attaching one sensor unit to the test subject;
   guiding the test subject through a corresponding regimen consisting of a plurality of dynamic movements wherein the plurality of dynamic movements comprise at least two dynamic movements different from one another and wherein the plurality of dynamic movements are in addition to or different than walking, jogging, or running;
   measuring movement of a portion of the test subject supported by or within said garment with the sensor along each of an X, Y, and Z axis according to Cartesian coordinates;

calculating a change in position along each of the X, Y, and Z axis during the regimen;

assigning a support value to the garment based on at least one change value calculated.

2. The method of claim 1, wherein the garment is a sports bra and bust movement during the regimen is measured for determining whether the support value of the sports bra is low, medium, or high.

3. The method of claim 1, wherein the sensor unit is in communication with a controller configured to receive data from the sensor for calculating the change along each of the X, Y, and Z axis.

4. The method of claim 2, wherein the X axis correlates to side to side movement of the bust, the Y axis correlates to vertical movement of the bust, the Z axis correlates to backward and forward movement of the bust with respect to a torso of the test subject.

5. The method of claim 2, wherein the sensor unit comprises a position sensor, a linear position sensor, an accelerometer, a gyroscope or combination thereof.

6. The method of claim 2 wherein the one sensor unit is a single sensor unit removably secured to the test subject at above a left cup portion of the sports bra.

7. The method of claim 6, wherein the sensor unit is removably secured to the test subject by way of a left strap of the sports bra which holds a magnet in contact with the test subject.

8. The method of claim 1, wherein the corresponding regimen is one or more of a warm-up regimen, a low support regimen, a medium support regiment, and a high support regimen and wherein movement is measured by the sensor continuously during the corresponding regimen.

9. The method of claim 2, wherein calculating movement of the bust comprises calculating a greatest change in position or acceleration along each of the X, Y, and Z axis and assigning a support value to the sports bra is based on at least one greatest change value calculated.

10. The method of claim 9, wherein the support values comprise:
a low support sports bra wherein the greatest change value along at least the Y axis is greater than about 200;
a medium support sports bra wherein the greatest change value along at least the Y axis is in the range of about 100 to 200;
a high support sports bra wherein the greatest change value along at least the Y axis is less than about 100.

11. A method of testing and evaluating a sports bra for a level of support provided by the sports bra, the method comprising:
selecting a sports bra;
removably attaching one sensor unit to the sports bra worn by a wearer of the sports bra;
guiding the wearer of the sports bra through an exercise regimen corresponding to a first support level indicated for the sports bra;
measuring vertical, lateral and backward/forward movement of a bust supported by or within the sports bra with the sensor; and
determining if the first support level indicated for the sports bra is accurate,
wherein the exercise regimen corresponding to the first support level indicated for the sports bra comprises a plurality of dynamic movements wherein at least two of the plurality of dynamic movements in any regimen are different dynamic movements.

12. The method of claim 11 and further comprising updating to a second support level indicated wherein in the second support level is more accurate than the first support level.

13. The method of claim 12 and where updating is based in part upon the measured change in movement in at least one of the vertical, lateral and backward/forward directions a upper portion of a left cup of the sports bra.

14. The method of claim 12 and further comprising calculating a largest change in movement in each of the vertical, lateral and backward/forward directions throughout the exercise regimen.

15. The method of claim 11 wherein the exercise regimen corresponds to the first support level is one of a low support regimen, a medium support regimen, or a high support regimen.

16. The method of claim 15, wherein the exercise regimen also includes a warm-up regimen.

17. The method of claim 12, wherein each of the low support regimen, medium support regimen, and high support regimen comprise a plurality of dynamic movements wherein at least two of the plurality of dynamic movements in any regimen are different moves.

18. The method of claim 12, wherein each of the low support regimen, medium support regimen, and high support regimen comprise transitions between each dynamic move of a plurality of dynamic moves where the transitions comprise in the range of about 0 to about 15 seconds of rest.

19. The method of claim 17 wherein each of the low support regimen, medium support regimen, and high support regimen comprise a different combination of the plurality of dynamic movements.

20. The method of claim 11 wherein removably attaching one sensor unit to the wearer of the sports bra comprises removably attaching a single sensor unit to the sports bra at a location on the wearer at above a left cup portion of the sports bra.

* * * * *